United States Patent
Kramer et al.

(10) Patent No.: US 7,310,554 B2
(45) Date of Patent: Dec. 18, 2007

(54) METHOD AND APPARATUS FOR ADJUSTMENT OF SEQUENTIAL BIVENTRICULAR PACING PARAMETERS

(75) Inventors: Andrew P. Kramer, Stillwater, MN (US); Jiang Ding, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 749 days.

(21) Appl. No.: 10/742,630

(22) Filed: Dec. 19, 2003

(65) Prior Publication Data

US 2004/0193223 A1  Sep. 30, 2004

Related U.S. Application Data

(63) Continuation-in-part of application No. 10/352,780, filed on Jan. 28, 2003, now Pat. No. 7,013,176.

(51) Int. Cl.
 *A61N 1/00* (2006.01)
(52) U.S. Cl. ......................................................... 607/9
(58) Field of Classification Search ................ 607/15, 607/18, 9, 123, 25, 30, 32, 59, 60
See application file for complete search history.

(56) References Cited

U.S. PATENT DOCUMENTS

| | | | |
|---|---|---|---|
| 4,401,119 A | 8/1983 | Herpers | |
| 4,432,362 A | 2/1984 | Leckrone et al. | |
| 4,922,907 A | 5/1990 | Hedin et al. | |
| 4,957,115 A * | 9/1990 | Selker | 600/509 |
| 5,129,393 A * | 7/1992 | Brumwell | 607/9 |
| 5,168,869 A | 12/1992 | Chirife | |
| 5,188,106 A | 2/1993 | Nappholz et al. | |
| 5,312,452 A | 5/1994 | Salo | |
| 5,318,595 A | 6/1994 | Ferek-Petric et al. | |
| 5,330,511 A | 7/1994 | Boute | |
| 5,334,222 A | 8/1994 | Salo et al. | |
| 5,372,607 A * | 12/1994 | Stone et al. | 607/30 |
| 5,413,592 A | 5/1995 | Schroeppel | |

(Continued)

FOREIGN PATENT DOCUMENTS

EP  0474958  3/1992

(Continued)

OTHER PUBLICATIONS

"International Search Report, for Application No. PCT/US2004/042496, date mailed Jun. 7, 2005", 13 Pages.

(Continued)

*Primary Examiner*—Mark Bockelman
(74) *Attorney, Agent, or Firm*—Schwegman, Lundberg & Woessner, P.A.

(57) ABSTRACT

A method and system are disclosed for setting the pacing parameters utilized by an implantable cardiac device in delivering cardiac resynchronization therapy. The system may, in different embodiments, be implemented in programming of the implantable device and an external programmer in communication therewith or in the programming of the implantable device by itself. The selection of the pacing parameters is based at least in part upon measurements of intrinsic cardiac conduction parameters. Among the pacing parameters which may be selected in this way are the atrio-ventricular delay interval used in atrial-tracking and AV sequential pacing modes and the biventricular offset interval.

20 Claims, 8 Drawing Sheets

U.S. PATENT DOCUMENTS

| | | | |
|---|---|---|---|
| 5,417,717 A | 5/1995 | Salo et al. | |
| 5,466,245 A | 11/1995 | Spinelli et al. | |
| 5,487,752 A | 1/1996 | Salo et al. | |
| 5,514,163 A | 5/1996 | Markowitz et al. | |
| 5,527,347 A | 6/1996 | Shelton et al. | |
| 5,534,016 A | 7/1996 | Boute | |
| 5,540,727 A | 7/1996 | Tockman et al. | |
| 5,549,650 A | 8/1996 | Bornzin et al. | |
| 5,554,177 A | 9/1996 | Kieval et al. | |
| 5,584,867 A | 12/1996 | Limousin et al. | |
| 5,584,868 A | 12/1996 | Salo et al. | |
| 5,609,612 A | 3/1997 | Plicchi et al. | |
| 5,626,620 A | 5/1997 | Kieval et al. | |
| 5,626,623 A | 5/1997 | Kieval et al. | |
| 5,628,777 A | 5/1997 | Moberg et al. | |
| 5,690,689 A | 11/1997 | Sholder | |
| 5,700,283 A | 12/1997 | Salo | |
| 5,713,930 A | 2/1998 | van der Veen et al. | |
| 5,713,933 A | 2/1998 | Condie et al. | |
| 5,716,383 A | 2/1998 | Kieval et al. | |
| 5,749,906 A | 5/1998 | Kieval et al. | |
| 5,800,471 A | 9/1998 | Baumann | |
| 5,836,987 A | 11/1998 | Baumann et al. | |
| 5,891,176 A | 4/1999 | Bornzin | |
| 6,058,329 A | 5/2000 | Salo et al. | |
| 6,144,879 A | 11/2000 | Gray | |
| 6,144,880 A | 11/2000 | Ding et al. | |
| 6,208,901 B1 | 3/2001 | Hartung | |
| 6,280,389 B1 | 8/2001 | Ding et al. | |
| 6,285,907 B1 * | 9/2001 | Kramer et al. | 607/9 |
| 6,311,089 B1 | 10/2001 | Mann et al. | |
| 6,430,439 B1 | 8/2002 | Wentkowski et al. | |
| 6,438,421 B1 | 8/2002 | Stahmann et al. | |
| 6,449,510 B1 | 9/2002 | Albers et al. | |
| 6,480,742 B2 | 11/2002 | Stahmann et al. | |
| 6,507,756 B1 | 1/2003 | Heynen et al. | |
| 6,512,952 B2 | 1/2003 | Stahmann et al. | |
| 6,522,921 B2 | 2/2003 | Stahmann et al. | |
| 6,522,923 B1 | 2/2003 | Turcott | |
| 6,553,258 B2 | 4/2003 | Stahmann et al. | |
| 6,757,562 B2 | 6/2004 | Baker et al. | |
| 2002/0123769 A1 | 9/2002 | Panken et al. | |
| 2002/0183795 A1 | 12/2002 | Rouw et al. | |
| 2003/0083704 A1 | 5/2003 | Baker et al. | |
| 2003/0105496 A1 | 6/2003 | Yu et al. | |
| 2003/0199930 A1 * | 10/2003 | Grandjean | 607/9 |
| 2003/0233131 A1 | 12/2003 | Kramer et al. | |
| 2004/0147966 A1 | 7/2004 | Ding et al. | |

FOREIGN PATENT DOCUMENTS

| | | |
|---|---|---|
| EP | 0970721 A2 | 1/2000 |
| WO | WO-9958191 A1 | 11/1999 |
| WO | WO2004-011088 A1 | 2/2004 |

OTHER PUBLICATIONS

Auricchio, A., et al., "Acute Hemodynamic Improvement by Pacing in Patients with Severe Congestive Heart Failure", *PACE*, vol. 20 (*Part 1*), (Feb. 1997), 313-324.

Auricchio, A., et al., "Can the optimum dosage of resynchronization therapy be derived from the Intracardiac Electrogram?", *Journal of the American College of Cardiology*, vol. 39, *Supplement 1*, (Mar. 6, 2002), 124.

Auricchio, Angelo, et al., "Effect of pacing chamber and atrioventricular delay on acute systolic function of paced patients with congestive heart failure. The Pacing Therapies for Congestive Heart Failure Study Group. The Guidant Congestive Heart Failure Research Group", *Circulation*, 99(23), (Jun. 15, 1999), 2993-3001.

Blanc, J. J., "Evaluation of Different Ventricular Pacing Sites in Patients With Severe Heart Failure", *Circulation*, vol. 96, No. 10, (Nov. 18, 1997), 3273-3277.

Brecker, Stephen et al., "Effects of dual-chamber pacing with short atrioventricular delay in dilated cardiomyopathy", *Lancet*, vol. 340, (1992), 1308-1312.

Butter, C., et al., "Non-Simultaneous Biventricular stimulation: A new paradigm of ventricular resynchronization therapy for heart failure patients", *PACE*, vol. 23 (*Part II*), *Abstact*, (2000), 589.

Fried, Ari G., "Electrical and Hemodynamic Correlates of the Maximal Rate of Pressure Increase in the Human Left Ventricle", *Journal of Cardiac Failure*, vol. 5, No. 1, (Mar. 1999), 8-16.

Kass, David A., "Improved Left Ventricular Mechanics From Acute VDD Pacing in Patients with Dilated Cardiomyopathy and Ventricular Conduction Delay", *Circulation*, 99(12), (Mar. 30, 1999), 1567-1573.

Nishimura, R. A., et al., "Mechanism of hemodynamic improvement by dual-chamber pacing for severe left ventricular dysfunction: An acute Doppler and catheterization hemodynamic study", *Journal of the American College of Cardiology*, 25(2), (Feb. 1995), 281-288.

Ritter, P., et al., "A Built-In System Based on the Peak Endocardial Acceleration (PEA) for AV-Delay Optimization in DDDR Pacing", *PACE*, 20(5) (*Part II*), (Abstract of Paper presented at EUROPACE '97),(May 1997), p. 1567.

Xiao, H. B., et al., "Nature of ventricular activation in patients with dilated cardiomyopathy: evidence for bilateral bundle branch block", *Br Heart J.*, vol. 72, (1994), 167-174.

* cited by examiner

METHOD AND APPARATUS FOR ADJUSTMENT OF SEQUENTIAL BIVENTRICULAR PACING PARAMETERS

RELATED APPLICATIONS

This application is a continuation-in-part of U.S. patent application Ser. No. 10/352,780, filed on Jan. 28, 2003, now issued as U.S. Pat. No. 7,013,176, the disclosure of which is incorporated by reference.

FIELD OF THE INVENTION

This invention pertains to cardiac rhythm management devices such as pacemakers and other implantable devices for treating cardiac dysfunction.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction.

Pacing therapy can also be used in the treatment of heart failure, which refers to a clinical syndrome in which an abnormality of cardiac function causes a below normal cardiac output that can fall below a level adequate to meet the metabolic demand of peripheral tissues. When uncompensated, it usually presents as congestive heart failure due to the accompanying venous and pulmonary congestion. Heart failure can be due to a variety of etiologies with ischemic heart disease being the most common. It has been shown that some heart failure patients suffer from intraventricular and/or interventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection of an intrinsic atrial contraction. Appropriate specification of these pacing parameters is necessary in order to achieve optimum improvement in cardiac function, and it is this problem with which the present invention is primarily concerned.

SUMMARY

The present invention relates to a system and method for optimally determining pacing parameters for delivering cardiac resynchronization therapy. The system may include an implantable cardiac rhythm management device and an external programmer in communication therewith or the implantable device alone. In accordance with the invention, the system measures one or more intrinsic conduction parameters from electrogram signals generated during intrinsic beats. Optimum pre-excitation timing parameters may then be determined in accordance with formulas that relate the optimum pre-excitation timing parameter to the measured intrinsic conduction parameters as defined by a set of specified coefficients. The specified coefficients may be pre-derived from a linear regression analysis of clinical population data relating particular values of the measured intrinsic conduction parameters to an optimum value of the pre-excitation timing parameter as determined by concurrent measurement of another parameter reflective of cardiac function. Pre-excitation timing parameters which may be optimally determined in this manner are the biventricular offset interval which separates right and left ventricular paces and the atrio-ventricular delay interval used in atrial-tracking or AV sequential pacing.

DETAILED DESCRIPTION

Applying cardiac resynchronization therapy in the most efficacious manner requires optimal selection of a number of pacing parameters. Described below is a cardiac rhythm management device configurable for delivering resynchronization pacing to the left ventricle (LV) and/or the right ventricle (RV) in order to compensate for ventricular conduction delays and improve the coordination of ventricular contractions. In accordance with the present invention, a number of these parameters may be set or adjusted based upon measurements of intra-cardiac conduction times using the sensing channels of an implanted device. Algorithms for setting these pacing parameters may be implemented in either the programming of an external programmer or in the programming of the implanted device itself or as a printed lookup table procedure. In the former embodiment, the external programmer communicates with the implantable device over a telemetry link and receives either raw electrogram data, markers corresponding to particular sensed events, or measurements of the intervals between particular sensed events as computed by the implantable device. The external programmer may then compute optimal settings for pacing parameters which are either transmitted to the implantable device for immediate reprogramming or presented to a clinician operating the external programmer as recommendations. In another embodiment, the implantable device is programmed to automatically set certain pacing parameters in accordance with information gathered from its sensing channels. Among the pacing parameters which may be set by either of these embodiments are the selection of which heart chambers are to be paced, the atrio-ventricular delay interval, the biventricular offset interval, and selection between alternative LV pacing sites.

1. Exemplary Device Description

Conventional cardiac pacing with implanted pacemakers involves excitatory electrical stimulation of the heart by the delivery of pacing pulses to an electrode in electrical contact with the myocardium. The pacemaker is usually implanted subcutaneously on the patient's chest, and is connected to electrodes by leads threaded through the vessels of the upper venous system into the heart. An electrode can be incorporated into a sensing channel that generates an electrogram signal representing cardiac electrical activity at the electrode site and/or incorporated into a pacing channel for delivering pacing pulses to the site.

Figure 1:
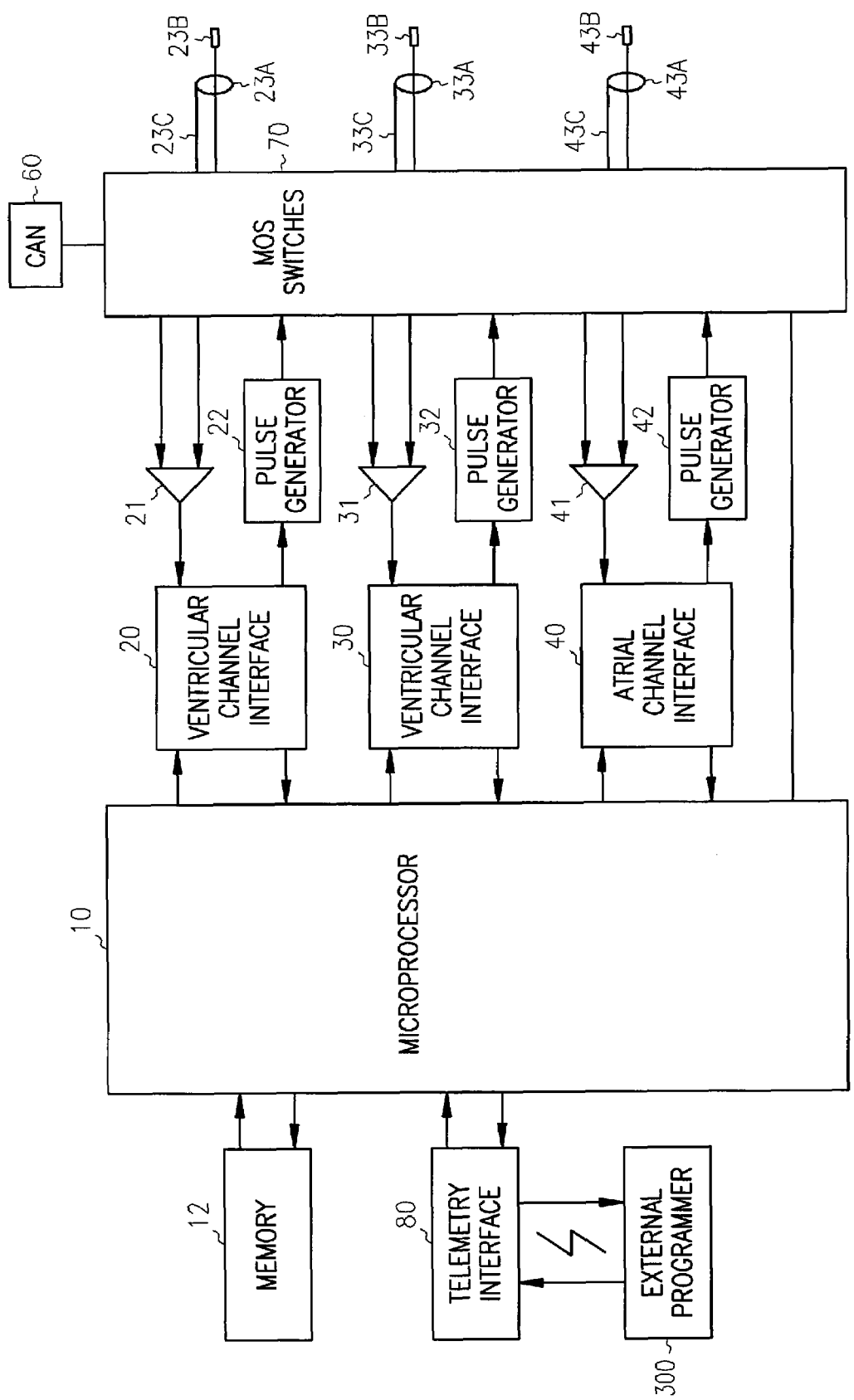
FIG. 1 is a block diagram of an exemplary cardiac device for practicing the present invention.

A block diagram of an implantable multi-site pacemaker having multiple sensing and pacing channels is shown in FIG. 1. (As the term is used herein, a "pacemaker" should be taken to mean any cardiac rhythm management device, such as an implantable cardioverter/defibrillator, with a pacing functionality.) The controller of the pacemaker is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to the code executed by a microprocessor. The controller is capable of operating the pacemaker in a number of programmed modes where a programmed mode defines how pacing pulses are output in response to sensed events and expiration of time intervals. A telemetry interface 80 is provided for communicating with an external programmer 300. The external programmer is a computerized device with an associated display and input means that can interrogate the pacemaker and receive stored data as well as directly adjust the operating parameters of the pacemaker. As described below, in certain embodiments of a system for setting pacing parameters, the external programmer may be utilized for computing optimal pacing parameters from data received from the implantable device over the telemetry link which can then be set automatically or presented to a clinician in the form of recommendations.

The embodiment shown in FIG. 1 has three sensing/pacing channels, where a pacing channel is made up of a pulse generator connected to an electrode while a sensing channel is made up of the sense amplifier connected to an electrode. A MOS switching network 70 controlled by the microprocessor is used to switch the electrodes from the input of a sense amplifier to the output of a pulse generator. The switching network 70 also allows the sensing and pacing channels to be configured by the controller with different combinations of the available electrodes. The channels may be configured as either atrial or ventricular channels allowing the device to deliver conventional ventricular single-site pacing with or without atrial tracking, biventricular pacing, or multi-site pacing of a single chamber. In an example configuration, a right atrial sensing/pacing channel includes ring electrode 43a and tip electrode 43b of bipolar lead 43c, sense amplifier 41, pulse generator 42, and a channel interface 40. A right ventricular sensing/pacing channel includes ring electrode 23a and tip electrode 23b of bipolar lead 23c, sense amplifier 21, pulse generator 22, and a channel interface 20, and a left ventricular sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In this embodiment, the device is equipped with bipolar leads that include two electrodes which are used for outputting a pacing pulse and/or sensing intrinsic activity. Other embodiments may employ unipolar leads with single electrodes for sensing and pacing. The switching network 70 may configure a channel for unipolar sensing or pacing by referencing an electrode of a unipolar or bipolar lead with the device housing or can 60.

The controller 10 controls the overall operation of the device in accordance with programmed instructions stored in memory. The controller 10 interprets electrogram signals from the sensing channels and controls the delivery of paces in accordance with a pacing mode. The sensing circuitry of the pacemaker generates atrial and ventricular electrogram signals from the voltages sensed by the electrodes of a particular channel. An electrogram is analogous to a surface EKG and indicates the time course and amplitude of cardiac depolarization and repolarization that occurs during either an intrinsic or paced beat. When an electrogram signal in an atrial or ventricular sensing channel exceeds a specified threshold, the controller detects an atrial or ventricular sense, respectively, which pacing algorithms may employ to trigger or inhibit pacing.

2. Cardiac Resynchronization Pacing Therapy

Cardiac resynchronization therapy is most conveniently delivered in conjunction with a bradycardia pacing mode. Bradycardia pacing modes refer to pacing algorithms used to pace the atria and/or ventricles in a manner that enforces a certain minimum heart rate. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval for pacing the ventricles can be defined between ventricular events, referred to as the cardiac cycle (CC) interval with its inverse being the lower rate limit or LRL. The CC interval is restarted with each ventricular sense or pace. In atrial tracking and AV sequential pacing modes, another ventricular escape interval is defined between atrial and ventricular events, referred to as the atrio-ventricular pacing delay interval or AVD, where a ventricular pacing pulse is delivered upon expiration of the atrio-ventricular pacing delay interval if no ventricular sense occurs before. In an atrial tracking mode, the atrio-ventricular pacing delay interval is triggered by an atrial sense and stopped by a ventricular sense or pace. An atrial escape interval can also be defined for pacing the atria either alone or in addition to pacing the ventricles. In an AV sequential pacing mode, the atrio-ventricular delay interval is triggered by an atrial pace and stopped by a ventricular sense or pace. Atrial tracking and AV sequential pacing are commonly combined so that the AVD starts with either an atrial pace or sense.

As described above, cardiac resynchronization therapy is pacing stimulation applied to one or more heart chambers in a manner that compensates for conduction delays. Ventricular resynchronization pacing is useful in treating heart failure in patients with interventricular or intraventricular conduction defects because, although not directly inotropic, resynchronization results in a more coordinated contraction of the ventricles with improved pumping efficiency and increased cardiac output. Ventricular resynchronization can be achieved in certain patients by pacing at a single unconventional site, such as the left ventricle instead of the right ventricle in patients with left ventricular conduction defects. Resynchronization pacing may also involve biventricular pacing with the paces to right and left ventricles delivered either simultaneously or sequentially, with the interval between the paces termed the biventricular offset (BVO) interval (also sometimes referred to as the LV offset (LVO) interval or VV delay). The offset interval may be zero in order to pace both ventricles simultaneously, or non-zero in order to pace the left and right ventricles sequentially. For one embodiment, the offset interval is signed, with a positive value indicating a pace to the left after the right and a negative value indicating a pace to the left before the right. For another embodiment, the offset interval is the unsigned difference between the atrioventricular pacing delay for the first paced ventricle and the atrioventricular pacing delay for the second paced ventricle.

Cardiac resynchronization therapy is most commonly applied in the treatment of patients with heart failure due to left ventricular dysfunction which is either caused by or contributed to by left ventricular conduction abnormalities. In such patients, the left ventricle or parts of the left ventricle contract later than normal during systole which thereby impairs pumping efficiency. In order to resynchronize ventricular contractions in such patients, pacing therapy is applied such that the left ventricle or a portion of the left ventricle is pre-excited relative to when it would become depolarized in an intrinsic contraction. Optimal pre-excitation in a given patient may be obtained with biventricular pacing or with left ventricular-only pacing.

3. Optimal Adjustment of Pre-Excitation Timing Parameters

Once a particular resynchronization pacing mode is selected for a patient, pacing parameters affecting the manner and extent to which pre-excitation is applied must be specified. Such pre-excitation timing parameters would include, for example, the atrio-ventricular pacing delay (AVD) and the biventricular offset interval. The biventricular offset interval determines the manner in which the left ventricle is pre-excited relative to right ventricular events. The length of the specified AVD relative to the intrinsic atrio-ventricular delay dictates how early in the cardiac cycle that pacing stimulation is first delivered to the ventricles and, therefore, the amount of pre-excitation delivered to the patient. In order to optimally specify these parameters, the patient may be subjected to clinical hemodynamic testing after implantation where the parameters are varied as cardiac function is assessed. For example, a patient may be given resynchronization stimulation while varying pre-excitation timing parameters in order to determine the values of the parameters that result in maximum cardiac performance, as determined by measuring a parameter reflective of cardiac function such as maximum left ventricular pressure change (dP/dt).

Determining optimal pacing parameters for an individual patient by clinical hemodynamic testing, however, is difficult and costly. It would be advantageous if such optimal pacing parameters could be determined from measurements of intrinsic conduction parameters which reflect how excitation is conducted within the patient's heart during intrinsic beats. In the approach of the present invention, therefore, intrinsic conduction data is collected from a surface EKG or from the sensing channels of the implantable cardiac resynchronization device and then used to compute optimum values of resynchronization pacing parameters. The technique for setting pacing parameters may be implemented as a system in which an external programmer presents intrinsic conduction data to a clinician who then manually programs the implantable device with parameters computed from the intrinsic conduction data (by, for example, using a printed lookup table and procedure). The technique may also be implemented as an automated system for setting optimal pacing parameters. The automated system may be made up of the implantable device alone or an external programmer in communication with the implantable device via a wireless telemetry link. The system may either automatically set the pacing parameters of the implantable device to the computed optimum values or present the optimum values to a clinician in the form of a recommendation. In one embodiment, one or more intrinsic conduction parameters is measured from electrogram signals generated by the sensing channels of an implantable cardiac resynchronization device during intrinsic beats, where the measured intrinsic conduction parameters may represent averages of values obtained during a specified number of intrinsic beats. The automated system, or a clinician manually programming the device, then computes a pre-excitation timing parameter such as the AVD or biventricular offset interval in accordance with a formula that equates an optimum value of the pre-excitation timing parameter to a linear sum of the measured intrinsic conduction parameters multiplied by specified coefficients.

In order to pre-derive the specified coefficients for later programming into the system or for use by a clinician, clinical population data is obtained that relates particular values of the measured intrinsic conduction parameters to an optimum value of the pre-excitation timing parameter as determined by concurrent measurement of another parameter reflective of cardiac function (e.g., maximum dP/dt or minimum atrial rate). A linear regression analysis is then performed to derive values of the specified coefficients used in the formula for setting the pre-excitation timing parameter, the specified coefficients thus being regression coefficients.

a. Optimal Adjustment of AVD

The AVD interval determines the amount of pre-excitation delivered by resynchronization, and its optimum value in any particular patient depends on the patient's intrinsic atrio-ventricular intervals and the degree of the patient's conduction pathology. The latter is related to the duration of ventricular depolarization during an intrinsic contraction as reflected by the QRS width in a surface electrocardiogram. It has been found empirically that patients can be categorized into two groups according to how well they respond to resynchronization therapy. It has also been found that patients can be identified as being in one group or another based upon their measured QRS widths. Strong responders, who exhibit a high degree of improvement in systolic function with resynchronization pacing, can be identified as patients with a QRS width greater than 150 milliseconds. Weak responders, who exhibit less improvement with resynchronization pacing, can be identified as patients with a QRS width less than or equal to 150 milliseconds. Within each of the two groups, a linear relationship has been found to exist between the optimal AVD interval for resynchronization pacing and the patient's measured intrinsic atrio-ventricular interval (AVI). Thus, in one embodiment, the optimum AVD interval may be determined by the following formulas:

$$AVD = a_1 AVI + a_2 \text{ (for QRS>150 milliseconds)}$$

or $$AVD = b_1 AVI + b_2 \text{ (for QRS<150 milliseconds)}$$

where the coefficients $a_1$, $a_2$, $b_1$, and $b_2$ are obtained from a regression analysis of representative population data. The intrinsic AV interval and QRS width can be determined either from a surface EKG or an intra-cardiac electrogram.

Categorizing patients into only two groups based upon QRS width necessarily has a limited sensitivity and specificity. It has further been found, however, that optimal AVD intervals for resynchronization pacing can be based upon a formula which is a continuous function of both QRS width (or other parameter reflective of depolarization duration) and the measured intrinsic AV delay interval. That is:

$$AVD = k_1 AVI + k_3 QRS + k_4$$

A further refinement of the above formula is to use separately measured intrinsic AV delay intervals for the right and left ventricles as could be obtained from the right ventricular and left ventricular sensing channels of an implanted cardiac device:

$$AVD = k_1 AV_R + k_2 AV_L + k_3 QRS + k_4$$

where $AV_R$ is the intrinsic AV interval for the right ventricle and $AV_L$ is the intrinsic AV interval for the left ventricle.

As noted above, intrinsic conduction parameters for computing the optimum AV delay may be obtained from intra-cardiac electrograms generated by the implanted device's sensing channels. The system may therefore be programmed to measure intrinsic conduction parameters from electrogram signals and use them in a formula with coefficients obtained by linear regression as described above to compute the optimum AVD. The system may be programmed to automatically set the programmed AVD interval in accordance with the computed optimum AVD interval or to recommend to an operator of the external programmer that the programmed AVD interval be set to the computed optimum AVD interval. The measured intrinsic conduction parameters may constitute either single measurements or averages of a plurality of measurements.

Figure 2:
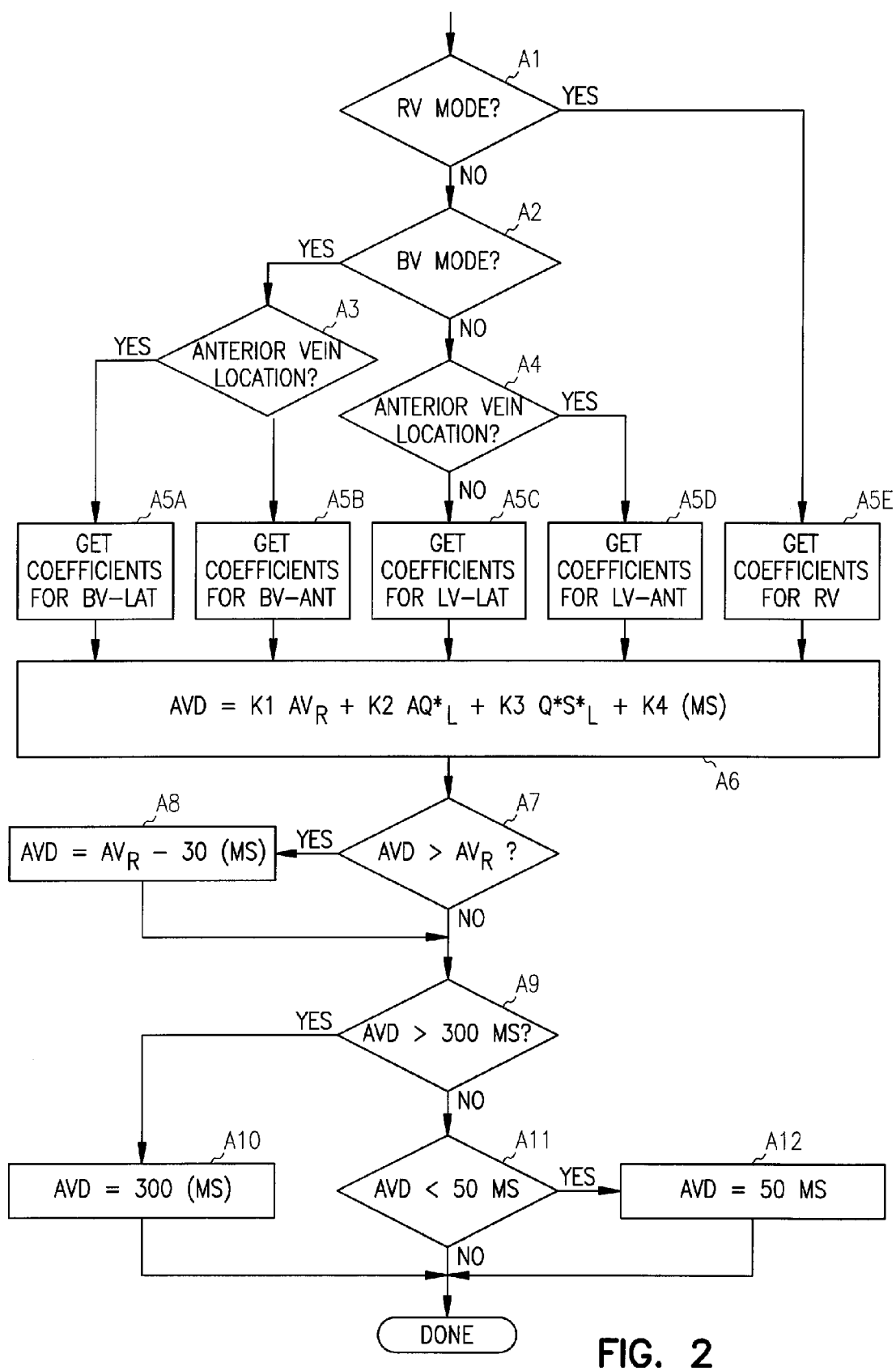
FIG. 2 illustrates an exemplary algorithm for calculating the atrio-ventricular delay interval used in atrial-tracking and AV sequential pacing modes.

FIG. 2 illustrates an exemplary implementation of the above-described method for determining the optimum AVD as could be executed by an appropriately programmed processor of the implantable cardiac device or external programmer. In this embodiment, the optimum AVD is obtained according to the following formula:

$$AVD = k_1 AV_R + k_2 AQ^*_L + k_3 Q^* S^* + k_4$$

where $AV_R$ is the right intrinsic atrio-ventricular delay measured as the interval between an atrial sense and a right ventricular sense, $AQ^*_L$ is the left intrinsic atrio-ventricular delay measured as the interval between an atrial sense and the start of left ventricular depolarization in an electrogram, and $Q^*S^*$ is the duration of ventricular depolarization measured as the interval from the start of left ventricular depolarization to the end of left ventricular depolarization in an electrogram. The start and end of depolarization may be detected by the implantable device from an electrogram using a threshold criterion similar to that used for detecting chamber senses. The specified coefficients are $k_1$, $k_2$, $k_3$, and $k_4$, where different sets of coefficients are used depending upon which chambers are paced in the currently programmed mode and the location of the left ventricular pacing lead. Each set of specified coefficients may be derived by a regression analysis of clinical data relating the optimum AVD to the measured intrinsic conduction parameters using a pacing mode for pacing a particular chamber or chambers and using a particular location for the left ventricular pacing lead.

Still referring to FIG. 2, the system determines at steps A1 and A2 whether the implantable device is operating in a right ventricular-only pacing mode (RV mode), biventricular pacing mode (BV mode), or left ventricular-only pacing mode (LV mode). If in RV mode, specified coefficients for optimum setting of the AVD interval in that mode are obtained at step A5e. If in BV mode, the system determines at step A3 whether the left ventricular pacing lead is in an anterior or lateral ventricular location, the latter corresponding to the left ventricular free wall. If the left ventricular pacing lead is lateral, specified coefficients for optimum setting of the AVD in that situation are obtained at step A5a, while if the left ventricular pacing lead is anterior, specified coefficients for optimum setting of the AVD are obtained at step A5b. Similarly, if it is determined at step A2 that the device is operating in LV mode, the left ventricular pacing lead location is determined at step A4 so that specified coefficients for setting the AVD are obtained at either step A5c or A5d in accordance with whether the left ventricular pacing lead location is lateral or anterior, respectively. The calculated AVD value is next compared with the right intrinsic atrio-ventricular delay at step A7. If the calculated AVD value is greater than the right intrinsic atrio-ventricular delay, the AVD is set to the value of the latter plus a specified margin (in this case, 30 ms). At steps A9 through A12, the calculated AVD is compared with specified maximum and minimum limit values (300 and 50 ms, respectively, in this case). If the calculated AVD exceeds the maximum limit value, the AVD is set to the maximum limit value. If the calculated AVD is below the minimum limit value, the AVD is set to the minimum limit value. In an alternative embodiment, if the calculated AVD value is greater than the minimum of a fixed percentage of the right intrinsic atrio-ventricular delay (e.g., 70%) or a fixed value (e.g., 300 ms), the AVD is set to the shorter of the two values (i.e., either the fixed percentage of the intrinsic AV delay or the fixed value) or set to a minimum limit value if the calculated AVD is less than the minimum limit value.

Alternative formulas for calculating the AVD using different intrinsic conduction parameters may also be employed, examples of which are:

$$AVD = k_1 AV_R + k_2 AV_L + k_3 Q^*S^* + k_4$$

$$AVD = k_1 AV_R + k_2 Q^*S^* + k_3$$

$$AVD = k_1 AV_L + k_2 AV_R + k_3$$

$$AVD = k_1 AV_R + k_2 QRS + k_3$$

where $AV_L$ is the left intrinsic atrio-ventricular delay measured as the interval between an atrial sense and a left ventricular sense, and QRS is the width of the QRS complex as determined from a surface electrocardiogram. Which formula would produce the best results in a given situation would depend upon both the individual patient and the particular implanted device. Tables 1 through 3 show example values of specified coefficients for calculating the AVD interval using three of the different formulas discussed above. The coefficients for each formula were calculated by a linear regression analysis of data obtained from a particular clinical population relating the optimum AVD to the intrinsic conduction parameters of the formula. In the tables, the suffix appended to the pacing mode denotes the left ventricular pacing site, either anterior (Ant) or the lateral free wall (Fwl).

TABLE 1

(AVD = k1 · AVI$_L$ + k2 · AVI$_R$ + k3)

| | k1 | k2 | k3 |
|---|---|---|---|
| LV-Ant | 0.163 | 0.769 | −59.6 |
| BV-Ant | 0.063 | 1.008 | −73.0 |
| LV-Fwl | −0.099 | 0.988 | −64.3 |
| BV-Fwl | −0.126 | 0.857 | −27.5 |

TABLE 2

(AVD = k1 · QRS + k2 · AVI$_R$ + k3)

| | k1 | k2 | k3 |
|---|---|---|---|
| LV-Ant | −1.325 | 0.918 | 135.3 |
| BV-Ant | −0.835 | 1.041 | 49.0 |
| LV-Fwl | −0.459 | 0.911 | −4.3 |
| BV-Fwl | −0.728 | 0.757 | 71.3 |

TABLE 3

(AVD = k1 · Q*S* + k2 · AQ* + k3 · AVI$_R$ + k4)

| | k1 | k2 | k3 | k4 |
|---|---|---|---|---|
| LV-Ant | −0.677 | 0.808 | 0.273 | 67.5 |
| BV-Ant | −0.706 | 0.615 | 0.610 | 47.2 |
| LV-Fwl | −0.337 | 0.157 | 0.797 | −0.46 |
| BV-Fwl | −0.312 | 0.339 | 0.482 | 31.6 |

The optimum AVD interval may, in certain instances, differ depending upon whether the ventricular pace or paces are delivered after an atrial sense or after an atrial pace (i.e., whether the paces are delivered in accordance with an atrial tracking mode or an AV sequential pacing mode). It may therefore be desirable to compute separate optimum AVD intervals for the two types of pacing which the implantable device may then use depending upon whether the AVD is initiated by an atrial sense or an atrial pace. Thus, with any of the formulas described above, an optimum AVD delay for use following an atrial pace may be computed with an intrinsic AV interval or intervals measured after an atrial pace, while an optimum AVD delay for use following an atrial sense may be computed with an intrinsic AV interval or intervals measured after an intrinsic atrial beat.

b. Optimal Adjustment of Biventricular Offset Interval

As described above, the amount of pre-excitation relative to an atrial beat that is provided to one or both ventricles by resynchronization pacing is determined by the AVD interval. Although it is believed that a primary factor in optimizing ventricular resynchronization pacing is optimal selection of the AVD interval, many patients exhibit further improvement in systolic function with optimal selection of a biventricular offset (BVO) interval (also referred to as the LV offset interval). That is, although certain patients may exhibit optimum improvement with either LV-only pacing (i.e., where only the left ventricle is pre-excited with the right ventricle being intrinsically activated via conduction through the AV node) or biventricular pacing with an arbitrarily chosen biventricular offset, others require biventricular offset pacing with an optimized biventricular offset for optimum improvement in systolic function. For this latter group of patients, it has been found that there is a predictive relationship between the intrinsic right-to-left ventricle conduction time and the best biventricular offset. Preferably, the relationship is expressed as a linear formula:

$$BVO = k1 \cdot \Delta_{RL} + k2$$

where BVO is the optimal biventricular offset interval, $\Delta_{RL}$ is the measured intrinsic right-to-left ventricle conduction time, and k1 and k2 are specified coefficients obtained empirically. Applying this formula results in an optimized biventricular offset for those patients who require it in order to achieve maximum improvement in systolic function with resynchronization pacing.

The $\Delta_{RL}$ parameter may be obtained from electrogram signals generated by the right and left ventricular sensing channels of the implantable device. The $\Delta_{RL}$ parameter may be obtained by the implantable device measuring the time interval between right and left ventricular senses, by the external programmer computing the time interval between RV and LV senses from an electrogram or sense markers transmitted from the implantable device, or by a clinician measuring the distance between RV and LV sense markers in an electrogram display generated by the external programmer. An estimate of the $\Delta_{RL}$ parameter may be measured by other means and used in a linear equation with different coefficients to predict the optimum biventricular offset. Specific estimates of the $\Delta_{RL}$ include the duration of the QRS interval measured on a surface ECG or on a leadless ECG recording from the implanted device, and the Q*S* interval measured from an intracardiac lead electrogram as the interval from the start of left ventricular depolarization to the end of left ventricular depolarization in the electrogram. The $\Delta_{RL}$ parameter may be either a single measurement or an average measurement taken over a number of beats. In one representative patient population, the following formula was found to calculate an optimum biventricular offset interval:

$$BVO = -0.333 \cdot \Delta_{RL} - 20$$

where the specified coefficients were obtained by a regression analysis, and the convention is adopted that a positive $\Delta_{RL}$ value represents the LV sense lagging the RV sense. The system may be programmed to automatically set the programmed biventricular offset interval in accordance with the computed optimum biventricular offset interval or to recommend to an operator of the external programmer that the programmed biventricular offset interval be set to the computed optimum biventricular offset interval.

Figure 7:
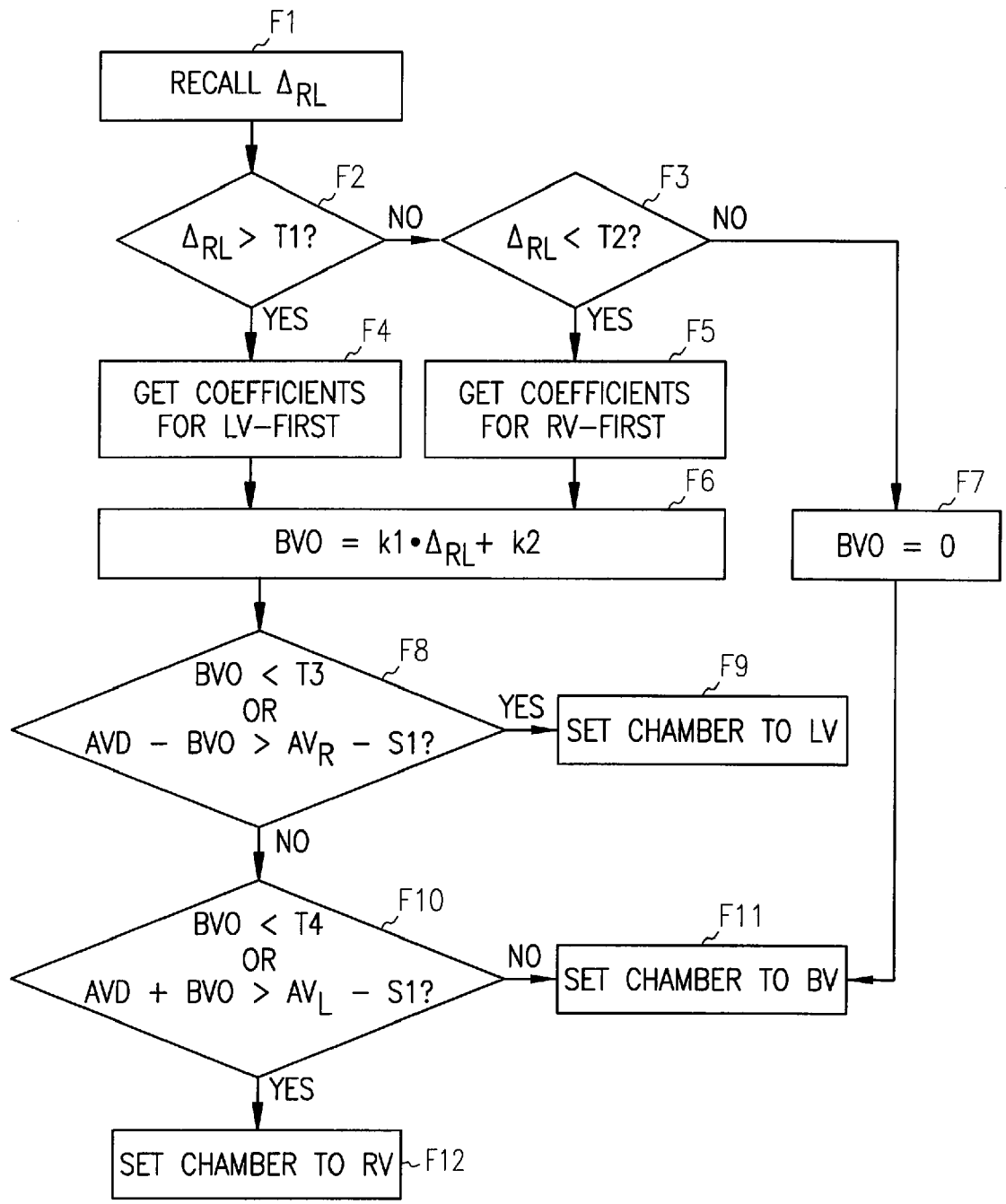
FIG. 7 illustrates an exemplary algorithm for determining an optimal biventricular offset interval.

FIG. 7 illustrates as steps F1 through F12 an exemplary implementation of the above-described method for determining the optimum biventricular offset interval as could be executed by an appropriately programmed processor of the implantable cardiac device or external programmer. In this embodiment, the optimum BVO is obtained according to the following formula:

$$BVO = k1 \cdot \Delta_{RL} + k2$$

where $\Delta_{RL}$ is the interval between a right ventricular sense and a left ventricular sense on electrocardiograms. The ventricular sense may be detected by the implantable device from an electrogram using a threshold criterion similar to that used for detecting chamber senses. Alternative formulas for calculating the BVO using different interventricular conduction delay parameters may also be employed, examples of which are:

$$BVO = k1 \cdot QRS + k2$$

$$BVO = k1 \cdot Q*S* + k2$$

where QRS is the width width of the QRS complex as determined from a surface electrocardiogram and Q*S* is the duration of ventricular depolarization measured as the interval from the start of left ventricular depolarization to the end of left ventricular depolarization in an electrogram. The specified coefficients are k1 and k2, where different sets of coefficients are used depending upon the sign and magnitude of the $\Delta_{RL}$ value. For instance as illustrated in FIG. 7, if $\Delta_{RL}$ is larger than a threshold value, T1, a set of LV-first coefficients is used, otherwise if $\Delta_{RL}$ is less than a threshold value, T2, a set of RV-first coefficients is used. When $\Delta_{RL}$ is greater than T1, there is a right-to-left ventricular conduction delay that can be corrected by pacing the LV first and the RV second; therefore the LV-first coefficients provide a BVO for pacing the LV before the RV. When $\Delta_{RL}$ is less than T2, there is a left-to-right ventricular conduction delay that can be corrected by pacing the RV first and the LV second; therefore the RV-first coefficients provide a BVO for pacing the RV before the LV. Example LV-first coefficients based on population data are k1=−0.333 and k2=−20. Example RV-first coefficients based on population data are k1=0 and k2=0. Also different coefficient sets can be selected based on different locations of the left and right ventricular sensing leads. For example, there can be two LV-first coefficient sets: one to be used when the left ventricular lead is located near the LV septum and another to be used when the left ventricular lead is located near the LV lateral wall. Also different coefficient sets can be selected dependent on whether $\Delta_{RL}$ is measured when atrial sensing or when atrial pacing. When $\Delta_{RL}$ is between T1 and T2, the interventricular conduction delay is too small to be corrected with sequential biventricular pacing; so the BVO is set to zero for simultaneous biventricular pacing. Example threshold values based on population data are T1=20 ms and T2=−20 ms.

Still referring to FIG. 7, after the optimum BVO is calculated, the system selects which chambers are to be paced in delivering ventricular resynchronization. The system determines whether the BVO is smaller than a threshold T3 or if the difference of AVD and BVO is greater than the right intrinsic atrio-ventricular delay ($AV_R$) less an offset S1, and in either case, selects the LV-only chamber for pacing. An example threshold value is T3=−80 ms. When BVO is less than this value, the conduction from the first LV pace is likely to spread to the right ventricle before it would be paced. Or the RV pace may occur after intrinsic conduction has spread to the right ventricle. This is indicated when the RV pace occurs after an offset S1 from the $AV_R$, where S1 may be for example between 0 and 30 ms. In either case, the effect of the sequential biventricular pacing is equivalent to LV-only pacing. Similarly, the system determines whether the opposite is true, that is whether the BVO is larger than a threshold T4 or if the sum of AVD and BVO is greater than the left intrinsic atrio-ventricular delay ($AV_L$), and in either case, selects the RV-only chamber for pacing. An example threshold value is T4=80 ms. If none of these exceptions occur, the system selects the biventricular chambers for pacing with the calculated biventricular offset interval.

3. Exemplary System for Determining Pre-Excitation Timing Parameters

A system made up of an implantable device and an external programmer (or the implantable device alone) may thus be programmed to determine optimum values for the AVD interval and the biventricular offset interval. In the following description of an exemplary embodiment, the system determines an optimum biventricular offset interval from measurement of the patient's $\Delta_{RL}$ conduction delay. The optimum AVD interval for use with the computed biventricular offset is either determined clinically or determined by the system from a formula utilizing conduction delay alone or combined with QRS width measurements as described above. Most patients with systolic dysfunction which can be improved by resynchronization therapy have conduction deficits which cause delayed intrinsic activation of the left ventricle (e.g., left bundle branch blocks). Systolic function is improved in these patients with resynchronization therapy that pre-excites the left ventricle. The formulas for computing an optimum AVD interval as described above then give an AVD interval representing the time between an atrial sense or pace and a left ventricular pace. The implantable device, however, may deliver ventricular paces in accordance with a pacing mode based upon right ventricular timing. In that case, the AVD interval used by the device is an escape interval started by an atrial sense or pace which is stopped by a right ventricular sense and results in a right ventricular pace upon expiration. In order to reconcile these two types of AVD intervals, the computed optimum biventricular offset is subtracted from the computed optimum AVD interval to give an AVD interval which can then be used by the implantable device with a pacing mode based upon right ventricular timing. For example, if the computed optimum biventricular offset were −20 ms (i.e., the LV pace leads the RV pace by 20 ms) and the computed optimum AVD interval for left ventricular pre-excitation were 100 ms (i.e., the time between an atrial sense or pace and a left ventricular pace is optimally 100 ms), then the actual AVD delay used by the implantable device using RV-based timing would be 100−(−20)=120 ms, which is the time between an atrial sense or pace and a right ventricular pace.

The steps performed by the system in this exemplary embodiment in order to select optimum pre-excitation timing parameters are as follows. First, the intrinsic $\Delta_{RL}$ parameter is determined, either automatically by the implanted device or external programmer or by manually measuring the interval from the implanted device's RV sense to LV sense event markers during intrinsic conduction on the electrogram display. In order to measure the intrinsic $\Delta_{RL}$ interval, the implantable device is set to a temporary sensing diagnostic mode, such as ODO mode. In the case where the system includes an external programmer, transmission of real-time atrial and ventricular markers to the external programmer is also enabled. After the device has transitioned into temporary sensing mode, the implantable device, or an operator of the external programmer, should wait for at least 10 cardiac cycles before measuring the intrinsic $\Delta_{RL}$ interval, and a typical measurement should be made when the intrinsic $\Delta_{RL}$ is stable. Averaging $\Delta_{RL}$ values from several cycles may be helpful. The following events must be avoided when making a measurement: ventricular pacing, intrinsic atrial rate above the programmed maximum tracking rate, premature ventricular contractions, and abnormal atrial or ventricular sensing. The same considerations may also apply when measuring any intrinsic conduction parameter. The intrinsic $\Delta_{RL}$ measurement is then used to calculate the optimum biventricular offset from a formula as described above or used to lookup an optimum biventricular offset from an equivalent table. Once the optimum biventricular offset is determined, an optimum AVD interval is calculated or otherwise obtained. The system may measure intrinsic AV conduction delays and the ventricular depolarization duration in order to compute the optimum AVD interval from a formula as described above. After determination of the optimum AVD interval, the biventricular offset may be subtracted from the optimum AVD interval to give a programmed AVD interval for use in RV-based pacing.

In certain instances, the system may modify the biventricular offset interval from its initially computed optimum value. For example, tachyarrhythmia detection based on right ventricular senses is affected by negative offset pacing of the left ventricle due to a cross-chamber sensing refractory period in the right ventricular sensing channel which is initiated by a left ventricular pace. (See U.S. patent application Ser. No. 10/037,444, filed on Oct. 25, 2001, the disclosure of which is hereby incorporated by reference.) That is, even while pacing the heart in a bradycardia resynchronization pacing mode, most cardiac rhythm management devices still monitor intrinsic cardiac activity for the onset of tachyarrhythmias. The device detects a ventricular tachyarrhythmia by measuring the time interval between successive ventricular depolarizations and comparing the measured interval to a specified limit value. That limit value is referred to as the tachyarrhythmia rate threshold interval (TRTI) and corresponds to the lowest intrinsic rate that is to be regarded as a tachyarrhythmia, referred to as the tachyarrhythmia rate threshold (TRT). The effective lower limit for tachyarrhythmia detection corresponds to a maximum tachyarrhythmia rate threshold interval MTRTI that may be expressed in terms of the pacing interval PI and the negative biventricular offset interval BVO as:

$$MTRTI=PI-BVO$$

Thus, decreasing the pacing interval and/or increasing the biventricular offset raises the lowest ventricular rate which can be detected as a tachyarrhythmia. The system may therefore be programmed to compare the maximum pacing rate (e.g., a maximum tracking rate in the case of an atrial tracking pacing mode or a maximum sensor indicated rate in the case of a rate-adaptive pacing mode) and the computed optimum biventricular offset interval to determine if tachyarrhythmia detection would be unduly compromised. The system may then either automatically shorten the biventricular offset interval or display a message advising the clinician to do so. For example, given a particular maximum tracking rate, the system may automatically shorten a computed biventricular offset interval so that the lowest ventricular rate detectable as a tachyarrhythmia is 5 bpm less than the programmed TRT parameter (or advise the clinician to do so via the external programmer).

The system may also incorporate logic for modifying the optimum biventricular offset interval after determination of the more important AVD interval. For example, the system might determine that a zero biventricular offset would be better for the patient. If a zero biventricular offset would be better, the system could either recommend that the biventricular offset be re-programmed to zero or automatically do so. This may be programmed to occur under any of the following circumstances: 1) positive biventricular offset has been programmed (when a positive biventricular offset should only be programmed as a result of direct hemodynamic testing or other evidence of effectiveness), 2) the system determines the patient is likely to be a weak responder or non-responder to CRT, as indicated by either a QRS<150 msec or a QRS<160 msec and the LV lead being in an anterior vein, indicating small baseline asynchrony, which requires a reduced degree of resynchronization that is delivered with longer AV delays resulting in fusion, or 3) the RV activation is delayed compared to the LV activation (i.e., the intrinsic $\Delta_{RL}$ is negative), suggesting a right bundle branch block pattern, which usually means the patient is a weak responder.

4. Optimal Adjustment of Right and Left Atrio-Ventricular Delays for Sequential Biventricular Pacing Another embodiment of a system for determining pre-excitation timing parameters for cardiac resynchronization therapy determines the biventricular offset interval by selecting two AVD intervals: 1) $AVD_{1ST}$, which is the atrio-ventricular delay to the first paced ventricle, and 2) $AVD_{2ND}$, which is the atrio-ventricular delay to the second paced ventricle. The difference between $AVD_{2ND}$ and $AVD_{1ST}$ is the biventricular offset interval, which is always a positive value. Either the right or left ventricle may be paced first. The optimum AVD intervals are either determined clinically or determined by the system from a formula utilizing conduction delay alone or combined with QRS width measurements as described above. In one case, the optimum AVD intervals are determined for atrial tracking, when the AV intervals are initiated by an atrial sense. In another case, the optimum AVD intervals are determined for AV sequential pacing, when the AV intervals are initiated by an atrial pace. In this embodiment, four optimum AV delay intervals are selected by the system and can be independently programmed into the implantable cardiac device by an external programmer: 1) right sensed AVD, 2) left sensed AVD, 3) right paced AVD, and 4) left paced AVD. When the left ventricle is paced first, left sensed and paced AVD intervals are set to the optimum sensed and paced $AVD_{1ST}$ intervals, and the right sensed and paced AVD intervals are set to the optimum sensed and paced $AVD_{2ND}$ intervals. The opposite assignments are made when the right ventricle is paced first.

Figure 8:
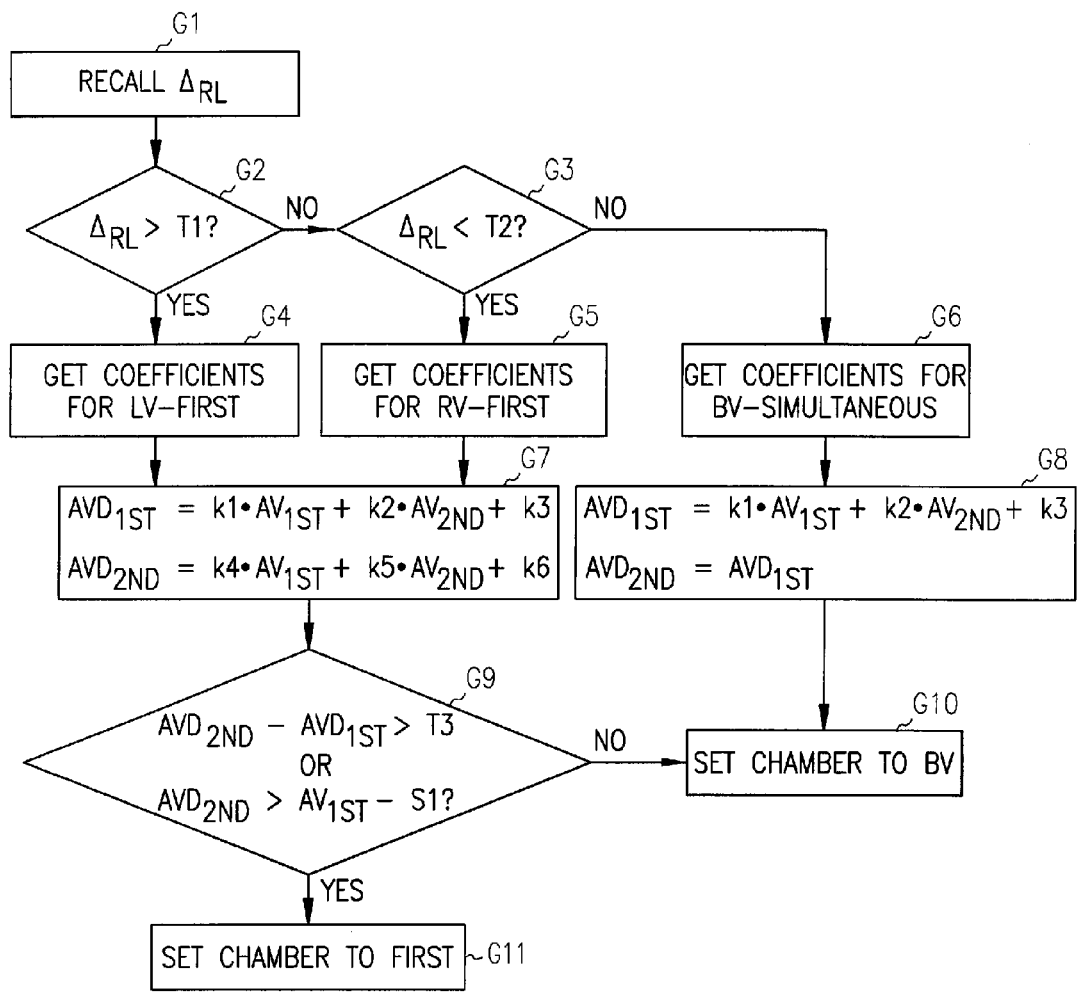
FIG. 8 illustrates an exemplary algorithm for determining separate atrio-ventricular delays for each ventricle.

FIG. 8 shows as steps G1 through G11 an exemplary method for determining the optimum $AVD_{1ST}$ and $AVD_{2ND}$ as could be executed by an appropriately programmed processor of the implantable cardiac device or external programmer. In this embodiment, the optimum AVD intervals are obtained according to the following formulas:

$$AVD_{1ST}=k1 \cdot AV_{1ST}+k2 \cdot AV_{2ND}+k3$$

$$AVD_{2ND}=k4 \cdot AV_{1ST}+k5 \cdot AV_{2ND}+k6$$

where $AV_{1ST}$ is the intrinsic interval between an atrial event (sensed or paced) and the right or left ventricular sense whichever is first, and $AV_{2ND}$ is the intrinsic interval between an atrial event and whichever is the second ventricular sense on electrocardiograms. Alternative formulas for calculating the AVD intervals may also be employed as illustrated in the section (Optimal adjustment of AVD) above. In the embodiment in FIG. 8, the coefficient sets (k1,k2,k3) and (k4,k5,k6) for the AVD interval formulas are based upon the sign and magnitude of the $\Delta_{RL}$ value, which is the right-to-left ventricular conduction delay. For instance as illustrated in FIG. 8, if $\Delta_{RL}$ is larger than a threshold value, T1, the left ventricle is selected to be paced first and a set of LV-first coefficients is used, otherwise if $\Delta_{RL}$ is less than a threshold value, T2, the right ventricle is selected to be paced first and a set of RV-first coefficients is used. Example LV-first coefficients for $AVD_{1ST}$ based on population data are presented in Table 1, and example coefficients for $AVD_{2ND}$ are shown in Table 4. Different coefficient sets can be selected based on different locations of the left and right ventricular sensing leads, as illustrated in the tables. Also different coefficient sets can be selected dependent on whether $\Delta_{RL}$ is measured when atrial sensing or when atrial pacing. When $\Delta_{RL}$ is between T1 and T2, the interventricular conduction delay is too small to be corrected with sequential biventricular pacing. In this case, the $AVD_{1ST}$ is calculated based on intrinsic conduction intervals and the $AVD_{2ND}$ is set equal to the $AVD_{1ST}$ for simultaneous biventricular pacing.

TABLE 4

| $(AVD_{2ND} = k4 \cdot AVI_L + k5 \cdot AVI_R + k6)$ | | | |
|---|---|---|---|
| | k4 | k5 | k6 |
| LV-Ant | 0.496 | 0.436 | −39.6 |
| BV-Ant | 0.396 | 0.675 | −53.0 |
| LV-Fwl | 0.234 | 0.655 | −44.3 |
| BV-Fwl | 0.207 | 0.524 | −7.5 |

Still referring to FIG. 8, after the optimum AVD intervals are calculated, the system selects which chambers are to be paced in delivering ventricular resynchronization. The system determines whether the biventricular offset interval is larger than a threshold T3 or if the $AVD_{2ND}$ is greater than the right intrinsic atrio-ventricular delay ($AV_R$) less an offset S1. In either case, the first-paced chamber only is selected for pacing. If neither is the case, the system selects the biventricular chambers for pacing with the calculated AVD intervals.

5. Adjustment of Other Pacing Parameters

Figure 3:
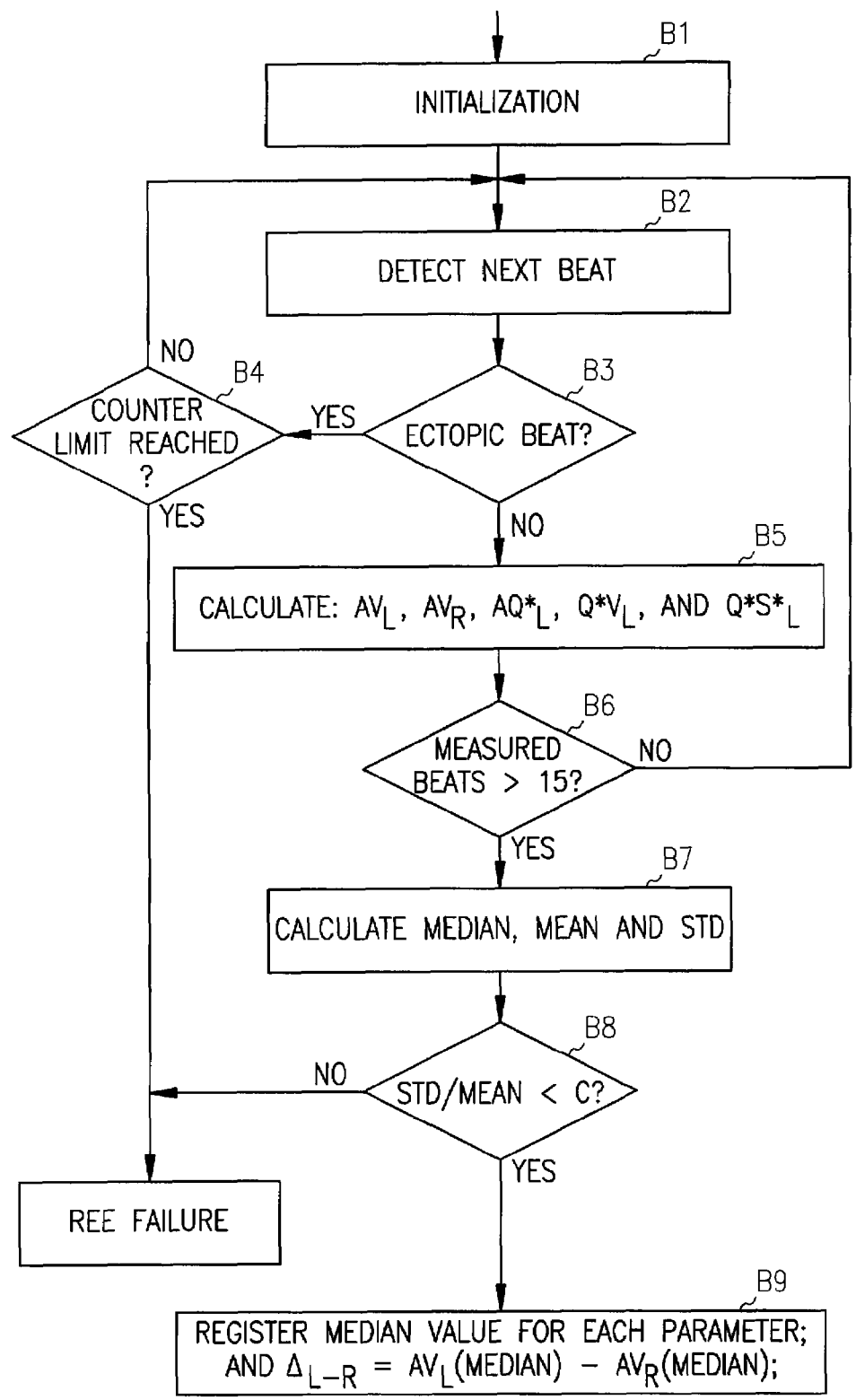
FIG. 3 illustrates an exemplary algorithm for measuring intrinsic conduction parameters.

FIG. 3 shows an exemplary algorithm for obtaining the intrinsic conduction parameters used to calculate the pre-excitation timing parameters by the procedures described above as well as select other optimum pacing parameters. (As the terms are used herein, "setting" or "selecting" a particular pacing parameter should be taken to mean either recommending the selected parameter to an operator of the external programmer or automatically configuring the implantable device with the selected parameter.) The algorithm would be executed during a data acquisition period while no pacing therapy is applied by the implantable device. At step B1, the sensing channels for obtaining the RV and LV electrograms are selected, and a beat counter variable is initialized. When an atrial sense occurs, a beat is detected at step B2 and the beat counter variable is incremented. If a subsequent ventricular sense does not occur, the beat is discarded as ectopic at step B3, and, if the beat counter variable does not exceed a specified limit value as tested for at step B4, the algorithm awaits the next beat detection at step B2. Otherwise the intrinsic conduction parameters $AV_L$, $AV_R$, $AQ^*_L$, $Q^*V_L$, and $Q^*S^*_L$ are measured from the RV and LV electrogram signals generated during the beat and stored at step B5. $AV_L$, $AV_R$, $AQ^*_L$, and $Q^*S^*_L$ are as defined above, and $Q^*V_L$ is the measured interval from the start of left ventricular depolarization to a left ventricular sense. At step B6, the beat counter variable is compared with another specified limit value (in this case, fifteen) and, if the limit value has not been reached, the algorithm waits for the next beat. After conduction parameters from fifteen beats have been stored, the mean, median, and standard deviation values of the parameter measurements are calculated at step B7. A step B8, the ratio of the standard deviation to the mean is calculated for all of conduction parameter measurements and compared to a specified limit value C, where in the case of $AV_L$ and $AV_R$, C=0.25, while in the case of $AQ^*_L$, $Q^*V_L$, and $Q^*S^*_L$, C=0.4. If the calculated ratios are all less than C, an average value of the stored measurement for each conduction parameter is registered and used to represent that conduction parameter at step B9. The average value of the stored measurements used in this embodiment is a median, but other embodiments may employ a mean, standard deviation, or similar statistic. In addition, an interventricular conduction delay parameter $\Delta_{L-R}$ is calculated as the difference between the average value of $AV_L$ and the average value of $AV_R$.

Figure 4:
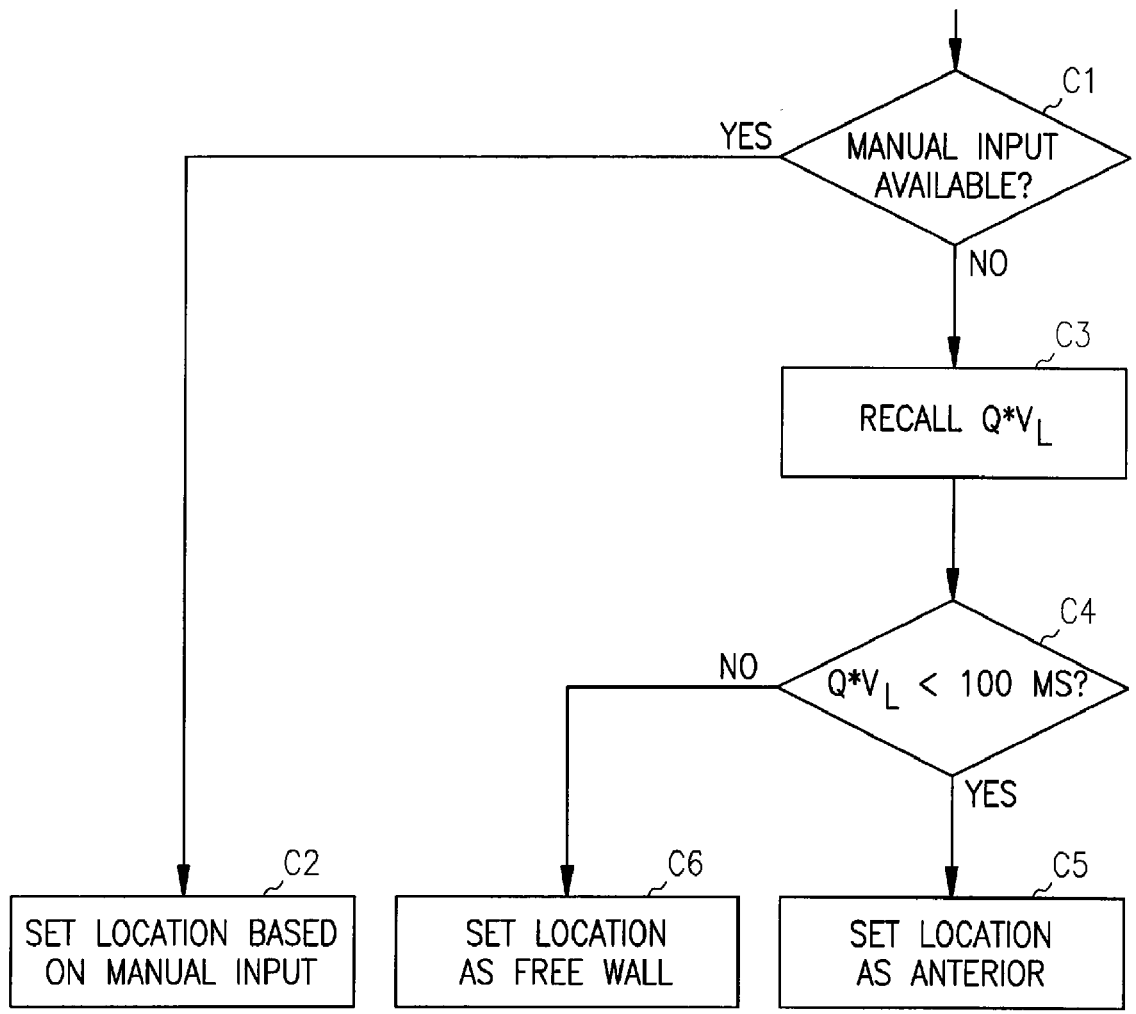
FIG. 4 illustrates an exemplary algorithm for determining the location of a left ventricular lead.

FIG. 4 illustrates an algorithm that may be executed by the system in order to determine the left ventricular lead location, which information is used by the algorithm for calculating the AVD illustrated in FIG. 2 If manual input of the parameter is available, as determined at step C1, the algorithm sets the lead location according to the manual input at step C2. Otherwise, the representative value of the $Q^*V_L$ parameter is recalled at step C3 and compared with a limit value (in this case, 100 ms) at step C4. If the $Q^*V_L$ parameter is less than the limit value, the lead location is set as anterior at step C5. Otherwise, the lead location is set as the left ventricular free wall at step C6.

The system may also use measured intrinsic conduction parameters to compute other pacing parameters for optimal delivery of therapy. Such parameters may include which heart chambers are to be paced and which alternative LV pacing sites should be used to pace the left ventricle. The left ventricular lead used for sensing and pacing may be a bipolar or multi-polar lead, which thus makes available to the implantable device alternative sites for delivering paces to the left ventricle. The selection between alternative LV pacing sites for optimal delivery of resynchronization therapy can be made based upon the relative intrinsic AV conduction delays measured from the different sites. Under most circumstances, it is desirable to pre-excite the left ventricular region that suffers the most conduction delay during an intrinsic contraction in order to compensate for that delay. For example, if two LV pacing sites L1 and L2 are available, the intrinsic conduction parameters $AV_{L1}$ and $AV_{LV2}$ can be measured which are the intervals between an atrial sense and a left ventricular sense detected from electrograms generated at sites L1 and L2, respectively. The pacing site which is excited later during an intrinsic beat as reflected by a longer AV delay interval can then be selected as the LV pacing site.

Figure 5:
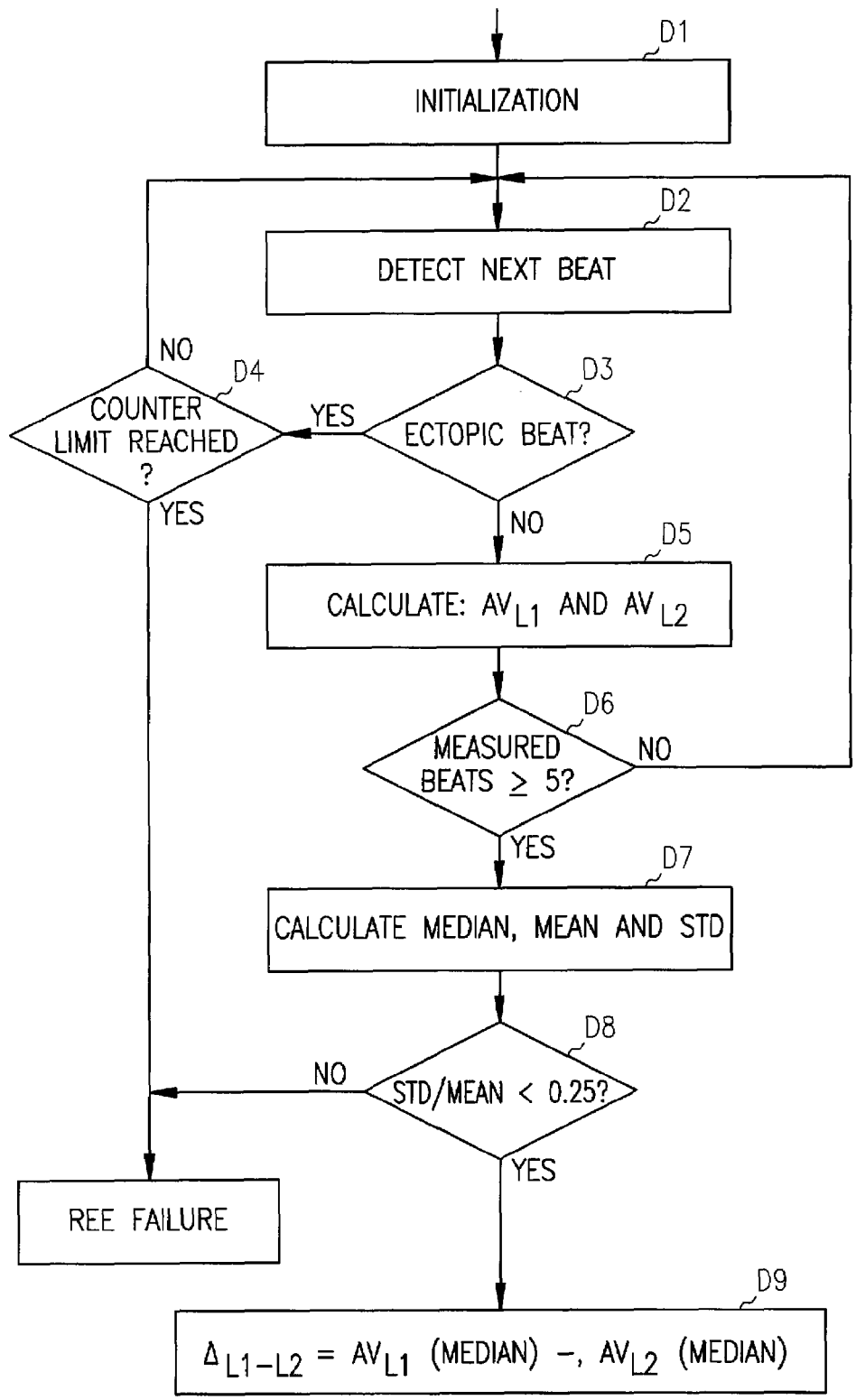
FIG. 5 illustrates an exemplary algorithm for measuring the relative intrinsic AV conduction delays at two left ventricular sites.
Figure 6:
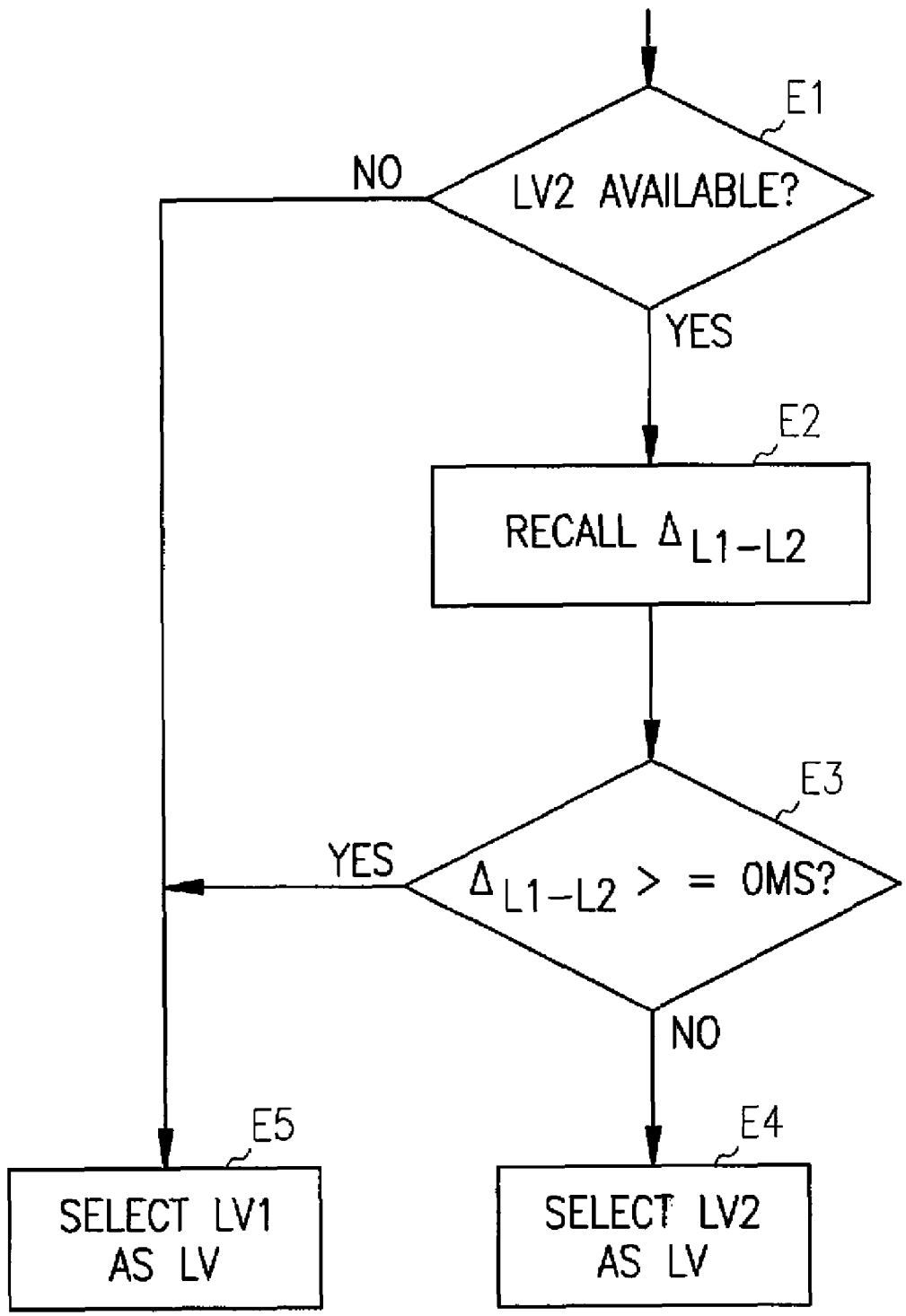
FIG. 6 illustrates an exemplary algorithm for selecting between two alternative left ventricular pacing sites.

FIG. 5 illustrates an exemplary algorithm for obtaining the $AV_{L1}$ and $AV_{LV2}$ parameters and calculating their difference, designated as $\Delta_{L1-L2}$. At step D1, the beat counter variable is reset, and the implantable device is configured to receive electrograms from alternative sites L1 and L2. In the particular device illustrated in FIG. 1, this would involve configuring two sensing channels with electrodes at the L1 and L2 sites via the switching network 70. Steps D2 through D4 discard ectopic beats and are similar to previously described steps B2 through B4 of FIG. 3. At step D5, the conduction parameters $AV_{L1}$ and $AV_{LV2}$ are measured from the two electrograms. At step D6, the beat counter variable is compared with another specified limit value (in this case, five) and, if the limit value has not been reached, the algorithm waits for the next beat. After measurements of the parameters from five beats have been stored, the mean, median, and standard deviation values of the $AV_{L1}$ and $AV_{LV2}$ measurements are calculated at step D7. At step D8, the ratio of the standard deviation to the mean is calculated and, if found to be less than a specified limit value (in this case, 0.25), $\Delta_{L1-L2}$ is calculated as the difference between the median values of $AV_{L1}$ and $AV_{LV2}$. The system may then be programmed to select the LV pacing site in accordance with the calculated $\Delta_{L1-L2}$ parameter, an exemplary procedure for which is illustrated by FIG. 6. At step E1, the system checks if a pacing site L2 is available and, if not, selects the default site L1 at step E5. If both sites L1 and L2 are available, the $\Delta_{L1-L2}$ parameter is recalled at step E2 and compared with zero at step E3. If $\Delta_{L1-L2}$ is negative, indicating that site L1 is excited earlier than site L2 during an intrinsic contraction, site L2 is selected as the LV pacing site at step E4. If $\Delta_{L1-L2}$ is greater than or equal to zero, indicating that site L1 is excited later than site L2 or at the same time, site L1 is selected as the LV pacing site at step E5.

6. System Implementation

The above-described algorithms may thus be used by a system including the implantable device and an external programmer or the implantable device alone in order to set one or more pacing parameters for the optimal delivery of resynchronization therapy. One or more of the algorithms may be executed by the system in order to initialize the parameters prior to delivering resynchronization therapy and/or executed periodically in order to update the parameters. The implantable cardiac rhythm management device would include sensing channels for generating electrogram signals corresponding to electrical activity in an atrium and both the right and left ventricles, right and left ventricular pacing channels for delivering pacing pulses to the right and left ventricles, and a controller for controlling the output of pacing pulses and interpreting electrogram signals, where the controller is programmed to pace at least one ventricle in a manner defined by at least one pre-excitation timing parameter. The system is programmed to measure (or enable measurement of) one or more intrinsic conduction parameters during an intrinsic beat from electrogram signals generated in the sensing channels of the implantable device, including an intrinsic atrio-ventricular delay interval in each ventricular sensing channel, a duration of ventricular depolarization, and a delay between right and left ventricular activation. The system may then be further programmed to select between a biventricular, right ventricular-only, or left ventricular-only pacing mode based upon the measured intrinsic conduction parameters and/or select the value of the pre-excitation timing parameter according to a formula which includes a linear combination of the measured intrinsic conduction parameters as defined by specified coefficients. The pre-excitation timing parameter may be the AVD and/or an offset interval for delivering biventricular or left ventricular-only pacing. The system may be further programmed to select between a biventricular, right ventricular-only, or left ventricular-only pacing mode based upon the measured intrinsic conduction parameters and a specified location of a left ventricular lead used by the left ventricular sensing and pacing channels, where the location of the left ventricular lead is specified by user input or determined from the value of $Q^*V_L$. The device may also be equipped with a plurality of sensing/pacing electrodes, sense amplifiers, pulse generators, and a switching network operated by the controller for configuring a sensing channel by connecting a selected electrode pair to a selected sense amplifier and for configuring a pacing channel by connecting a selected electrode pair to a selected pulse generator. The plurality of sensing/pacing electrodes may include at least two alternative left ventricular electrodes located at different left ventricular sites, and the measured intrinsic conduction parameters may include AV conduction delays measured from the at least two alternative left ventricular electrodes. The system may then be programmed to select between the alternative left ventricular electrodes for configuring the left ventricular pacing channel based upon the intrinsic AV conduction delays measured from each alternative left ventricular electrode such as by configuring the left ventricular pacing channel with whichever of the alternative left ventricular electrodes has the longest intrinsic AV conduction delay measured from it.

In one embodiment, the system for selecting optimum pacing parameters includes the implantable device and an external programmer in communication therewith. The processors of the implantable device and of the external programmer are programmed to perform the steps for selecting optimum pacing parameters as described above, where the computational burden may be shared between the two processors in any manner deemed to desirable. The implantable device may collect intrinsic conduction data and transmits the data to the external programmer in various alternative forms. For example, the transmitted intrinsic conduction data may constitute raw electrograms, markers representing particular events and the times of their occurrence, or the derived conduction parameters themselves. Processing of the intrinsic conduction parameters in order to compute optimum pacing parameters by the algorithms described above may then be done entirely by the external programmer or shared between the external programmer and the implantable device. After computation of the optimum pacing parameter values, the external programmer may then automatically program the implantable device with the computed optimum pacing parameter settings or present the optimum values to a clinician operating the external programmer in the form of a recommendation.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A system for setting one of more pacing parameters used by an implantable cardiac rhythm management device in delivering cardiac resynchronization therapy, comprising:

an implantable cardiac rhythm management device which includes: an atrial sensing channel for generating electrogram signals corresponding to electrical activity in an atrium; right and left ventricular sensing channels for generating electrogram signals corresponding to electrical activity in the right and left ventricles, respectively; right and left ventricular pacing channels for delivering pacing pulses to the right and left ventricles, respectively; a controller for controlling the output of pacing pulses and interpreting electrogram signals, wherein the controller is programmed to deliver a left ventricular pace and a right ventricular pace separated by a programmed biventricular offset interval in accordance with a demand pacing mode; and, a telemetry interface;

an external programmer with associated display and input means in communication with the implantable device via the telemetry interface;

wherein the system is programmed to generate signals from which the delay between right ventricular and left ventricular activation during an intrinsic beat, referred to as the $\Delta_{RL}$ interval, may be measured; and, wherein the system is programmed to compute an optimum biventricular offset interval in accordance with a formula which expresses the optimum biventricular offset interval as a function of the measured $\Delta_{RL}$ interval.

2. The system of claim 1 wherein the system is programmed to measure the $\Delta_{RL}$ interval from electrogram signals received by the implantable device.

3. The system of claim 1 wherein the controller of the implantable device is programmed to pace the ventricles within a programmable atrio-ventricular delay (AVD) interval after an atrial sense in an atrial-tracking mode or an atrial pace in an AV sequential pacing mode.

4. The system of claim 3 wherein the system is programmed to measure at least one intrinsic atrio-ventricular delay interval from electrogram signals during an intrinsic beat and compute an optimum AVD interval in accordance with a formula which expresses the optimum AVD interval as a function of the measured intrinsic atrio-ventricular delay interval.

5. The system of claim 4 wherein the system is programmed to measure right and left intrinsic atrio-ventricular delay intervals and a duration of ventricular depolarization from electrogram signals and wherein the formula for computing the optimum AVD interval includes a linear combination of the measured right and left intrinsic atrio-ventricular delays and the measured duration of ventricular depolarization.

6. The system of claim 5 wherein the right intrinsic atrio-ventricular delay is measured as the interval between an atrial sense and a right ventricular sense designated as $AV_R$, the left intrinsic atrio-ventricular delay is measured as the interval between an atrial sense and the start of left ventricular depolarization in an electrogram designated as $AQ^*_L$, the duration of ventricular depolarization is measured as the interval from the start of left ventricular depolarization to the end of left ventricular depolarization in an electrogram designated as $Q^*S^*$, and the formula for computing the optimum AVD is:

$$AVD = k_1 AV_R + k_2 AQ^*_L + k_3 Q^*S^* + k_4$$

where $k_1$, $k_2$, $k_3$, and $k_4$ are specified coefficients.

7. The system of claim 4 wherein a right intrinsic atrio-ventricular delay is measured as the interval between an atrial sense and a right ventricular sense designated as $AV_R$, a left intrinsic atrio-ventricular delay is measured as the interval between an atrial sense and a left ventricular sense designated as $AV_L$, and the formula for computing the AVD is:

$$AVD = k_1 AV_R + k_2 AV_L + k_3$$

where $k_1$, $k_2$, and $k_3$, are specified coefficients.

8. The system of claim 4 wherein the intrinsic atrio-ventricular delay is measured as the interval between an atrial sense and a right ventricular sense designated as AVR, a duration of ventricular depolarization is measured as the interval from the start of left ventricular depolarization to the end of left ventricular depolarization in an electrogram designated as $Q^*S^*$, and the formula for computing the optimum AVD is:

$$AVD = k_1 AV_R + k_2 Q^*S^* + k_3$$

where $k_1$, $k_2$, and $k_3$ are specified coefficients.

9. The system of claim 4 wherein specified coefficients defining a linear combination of the measured intrinsic atrio-ventricular delay interval and the measured duration of ventricular depolarization have been pre-derived from a linear regression analysis of clinical population data relating measured intrinsic atrio-ventricular delay intervals and measured durations of ventricular depolarization to an optimum AVD for delivering cardiac resynchronization therapy as determined by measurement of a cardiac function parameter.

10. The system of claim 4 wherein the system is programmed to automatically set the programmed AVD interval in accordance with the computed optimum AVD interval.

11. The system of claim 4 wherein the system is programmed to recommend to an operator of the external programmer that the programmed AVD interval be set to the computed optimum AVD interval.

12. The system of claim 1 wherein the formula for computing the optimum biventricular offset interval BVO is:

$$BVO = k_1 \Delta_{RL} + k_2$$

where $k_1$ and $k_2$ are specified coefficients.

13. The system of claim 12 wherein the specified coefficients defining the relationship between the optimum biventricular offset and the measured $\Delta_{RL}$ interval have been pre-derived from a linear regression analysis of clinical population data relating measured $\Delta_{RL}$ intervals to an optimum biventricular offset for delivering cardiac resynchronization therapy as determined by measurement of a cardiac function parameter.

14. The system of claim 12 wherein the formula for computing the optimum biventricular offset interval BVO is:

$$BVO = -.333(\Delta_{RL}) - 20.$$

15. The system of claim 1 wherein the system is programmed to automatically set the programmed biventricular offset interval in accordance with the computed optimum biventricular offset interval.

16. The system of claim 1 wherein the system is programmed to recommend to an operator of the external programmer that the programmed biventricular offset interval be set to the computed optimum biventricular offset interval.

17. The system of claim 1 wherein the measured $\Delta_{RL}$ interval represents an average measurement taken over a plurality of intrinsic beats.

18. The system of claim 1 wherein the computed optimum biventricular offset interval is modified in order to maintain a desired tachyarrhythmia rate threshold.

19. A method for computing an optimum biventricular offset interval for delivering biventricular pacing therapy, wherein the biventricular offset interval is the interval between right and left ventricular paces, comprising:

measuring a delay between right ventricular and left ventricular activation during an intrinsic beat, referred to as the $\Delta_{RL}$ interval; and, computing an optimum biventricular offset interval in accordance with a formula which expresses the optimum biventricular offset interval as a function of the measured $\Delta_{RL}$ interval.

20. The method of claim 19 wherein the formula for computing the optimum biventricular offset interval BVO is:

$$BVO = k_1(ARL) + k_2$$

where $k_1$ and $k_2$ are specified coefficients defining the relationship between the optimum biventricular offset and the measured $\Delta_{RL}$ interval which have been pre-derived from a linear regression analysis of clinical population data relating measured $\Delta_{RL}$ intervals to an optimum biventricular offset for delivering cardiac resynchronization therapy as determined by measurement of a cardiac function parameter.

* * * * *

UNITED STATES PATENT AND TRADEMARK OFFICE
CERTIFICATE OF CORRECTION

PATENT NO. : 7,310,554 B2  Page 1 of 1
APPLICATION NO. : 10/742630
DATED : December 18, 2007
INVENTOR(S) : Kramer et al.

It is certified that error appears in the above-identified patent and that said Letters Patent is hereby corrected as shown below:

On the title page, in field (74), in "Attorney, Agent, or Firm", in column 2, line 1, delete "Lundberg" and insert -- Lundberg, --, therefor.

In column 20, line 1, in Claim 8, delete "AVR," and insert -- $AV_R$, --, therefor.

In column 20, line 28, in Claim 12, delete "$k_1 \Delta_{RL})+k_2$" and insert -- $k_1(\Delta_{RL})+k_2$ --, therefor.

In column 21, line 3, in Claim 20, delete "$k_1(ARL)+k_2$" and insert -- $k_1(\Delta_{RL})+k_2$ --, therefor.

Signed and Sealed this

Thirteenth Day of May, 2008

JON W. DUDAS
*Director of the United States Patent and Trademark Office*